(12) United States Patent
Kim et al.

(10) Patent No.: US 11,865,300 B2
(45) Date of Patent: Jan. 9, 2024

(54) LIQUID MEDICINE INJECTION DEVICE

(71) Applicant: EOFLOW CO., LTD., Seongnam-si (KR)

(72) Inventors: Jesse Jaejin Kim, Seongnam-si (KR); Seung Ha Kim, Goyang-si (KR)

(73) Assignee: EOFlow Co., Ltd., Seongnam-si (KR)

( * ) Notice: Subject to any disclaimer, the term of this patent is extended or adjusted under 35 U.S.C. 154(b) by 0 days.

(21) Appl. No.: 17/652,627

(22) Filed: Feb. 25, 2022

(65) Prior Publication Data

US 2022/0288301 A1 Sep. 15, 2022

Related U.S. Application Data

(63) Continuation of application No. 16/342,950, filed as application No. PCT/KR2017/011378 on Oct. 16, 2017, now Pat. No. 11,291,764.

(30) Foreign Application Priority Data

Oct. 18, 2016 (KR) .......................... 10-2016-0135264

(51) Int. Cl.
*A61M 5/145* (2006.01)
*A61M 5/24* (2006.01)
(Continued)

(52) U.S. Cl.
CPC .......... *A61M 5/1452* (2013.01); *A61M 5/002* (2013.01); *A61M 5/2422* (2013.01); *A61M 5/31568* (2013.01); *A61M 5/31501* (2013.01); *A61M 2205/82* (2013.01)

(58) Field of Classification Search
CPC .. A61M 2205/0216; A61M 2205/0227; A61M 2205/0233; A61M 2205/33;
(Continued)

(56) References Cited

U.S. PATENT DOCUMENTS 6,110,148 A    8/2000  Brown et al.
8,729,912 B2   5/2014  Cefai et al.
(Continued)

FOREIGN PATENT DOCUMENTS

JP   2009-529999   8/2009
JP   2012-504760   2/2012
(Continued)

OTHER PUBLICATIONS

Notice of Allowance dated Mar. 28, 2018 in corresponding Korean Patent Application No. 10-2016-0135264; 2 pages.
(Continued)

*Primary Examiner* — Shefali D Patel
(74) *Attorney, Agent, or Firm* — Knobbe, Martens, Olson & Bear, LLP

(57) ABSTRACT

A liquid medicine injection device includes: a liquid medicine storage unit including a cylinder including a space configured to store liquid medicine therein and a discharge hole connected to the space, and a piston arranged inside the cylinder and moving toward the discharge hole depending on discharge of the liquid medicine; a first electrode on an outer surface of the cylinder; a second electrode on the outer surface of the cylinder, the second electrode facing the first electrode with the piston therebetween; and a circuit unit including a substrate electrically connected to the first electrode and the second electrode.

9 Claims, 7 Drawing Sheets

(51) Int. Cl.
*A61M 5/00* (2006.01)
*A61M 5/315* (2006.01)

(58) Field of Classification Search
CPC .. A61M 2205/3317; A61M 2205/3327; A61M 2205/3379; A61M 2205/3389; A61M 2205/50; A61M 2205/82; A61M 5/002; A61M 5/14; A61M 5/142; A61M 5/145; A61M 5/1452; A61M 5/168; A61M 5/172; A61M 5/24; A61M 5/2422; A61M 5/315; A61M 5/31501; A61M 5/31568
See application file for complete search history.

(56) References Cited

U.S. PATENT DOCUMENTS

| | | |
|---|---|---|
| 2006/0178633 A1 | 8/2006 | Garibotto et al. |
| 2009/0069756 A1 | 3/2009 | Larsen |
| 2015/0268656 A1 | 9/2015 | Bammer et al. |
| 2016/0296935 A1 | 10/2016 | Gao et al. |

FOREIGN PATENT DOCUMENTS

| | | |
|---|---|---|
| JP | 2015-512509 | 4/2015 |
| KR | 10-1495768 | 11/2009 |
| KR | 10-2010-0108015 | 10/2010 |
| KR | 10-2014-0101255 | 5/2014 |
| WO | WO 2015/059192 | 4/2015 |

OTHER PUBLICATIONS

Office Action dated Aug. 21, 2017 in corresponding Korean Patent Application No. 10-2016-0135264; 6 pages.

Extended Search Report for European Application No. 17861489 dated Mar. 11, 2020, in 8 pages.

Office Action for Japanese Application No. 2019-515984 dated Mar. 3, 2020, in 6 pages.

LIQUID MEDICINE INJECTION DEVICE

CROSS-REFERENCE TO RELATED APPLICATION

This application is a continuation of U.S. application Ser. No. 16/342,950, filed on Apr. 17, 2019 as the national stage application under 35 U.S.C. § 371 of PCT Application No. PCT/KR2017/011378, filed on Oct. 16, 2017, which claims priority to Korean Patent Application No. KR 10-2016-0135264, filed on Oct. 18, 2016. Each of the above applications is incorporated herein by reference in its entirety.

TECHNICAL FIELD

The present disclosure relates to a liquid medicine injection device.

BACKGROUND ART

Diabetes is a disease based on a metabolic disorder that occurs because of shortage of insulin, which is one of the hormones secreted from a pancreas. As one of the active treatments for diabetic patients, a method of injecting insulin into a human body may be used. An apparatus for injecting insulin may be used so as to inject insulin to the interior of the body such that insulin is suitable for a patient's blood sugar change.

Liquid medicine such as insulin is injected by a very small amount. In the case where an injected amount is much or less than a predetermined amount, not only it is difficult to expect an effect of treatment but also side effects may occur.

SUMMARY OF CERTAIN INVENTIVE ASPECTS

Provided is a liquid medicine injection device configured to precisely control an amount of liquid medicine provided to a user, or including a sensing structure configured to sense a defect such as a leakage of the liquid medicine. The above object is provided as an example and the scope of the present disclosure is not limited thereto.

According to an aspect of the present disclosure, a liquid medicine injection device includes: a liquid medicine storage unit including a cylinder including a space configured to store liquid medicine therein and a discharge hole connected to the space, and a piston arranged inside the cylinder and moving toward the discharge hole depending on discharge of the liquid medicine; a first electrode on an outer surface of the cylinder; a second electrode on the outer surface of the cylinder, the second electrode facing the first electrode with the piston therebetween; and a circuit unit including a substrate electrically connected to the first electrode and the second electrode.

The first electrode and the second electrode may extend in a direction that intersects with a liquid surface of the liquid medicine that contacts the piston.

One end of the first electrode may be adjacent to the discharge hole, and another end of the first electrode may extend away from the discharge hole, and one end of the second electrode may be adjacent to the discharge hole, and another end of the second electrode may extend away from the discharge hole.

The circuit unit may calculate displacement information of the piston based on a capacitance change between the first electrode and the second electrode.

The circuit unit may calculate an actual injected amount of the liquid medicine based on the displacement information of the piston.

The liquid medicine injection device may further include a pump connected to the discharge hole.

The liquid medicine injection device may further include: a case configured to receive the liquid medicine storage unit and the circuit unit; and an inner frame inside the case.

The case may include first ribs arranged in a lengthwise direction of the liquid medicine storage unit, and the inner frame may include second ribs facing the first ribs of the case with the liquid medicine storage unit between the first ribs and the second ribs.

The liquid medicine injection device may further include: a conductive member curved along an outer surface of the liquid medicine storage unit, wherein the conductive member may connect one of the first electrode and the second electrode to the circuit unit.

The inner frame may regulate a location of the conductive member.

These and/or other aspects and advantages will become apparent and more readily appreciated from the following description of the embodiments and claims, taken in conjunction with the accompanying drawings.

Since a liquid medicine injection device according to embodiments may accurately obtain movement information, that is, displacement information of a piston through at least two electrode sheets, and calculate an actual discharge amount of liquid medicine through the displacement information, an accurate liquid medicine control, etc. are possible. However, the scope of the present disclosure is not limited by this effect.

DETAILED DESCRIPTION OF CERTAIN ILLUSTRATIVE EMBODIMENTS

Figure 1:
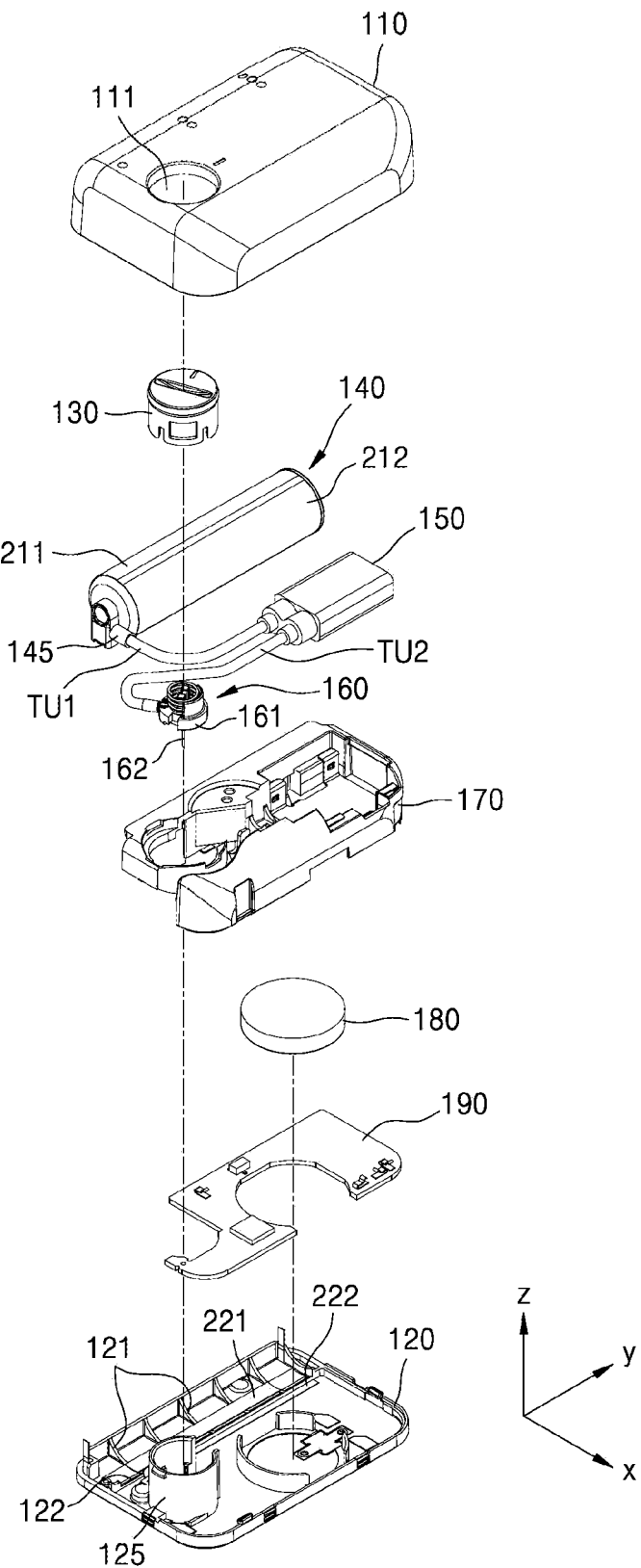
FIG. 1 is an exploded perspective view of a liquid medicine injection device according to an embodiment.

As the disclosure allows for various changes and numerous embodiments, example embodiments will be illustrated in the drawings and described in detail in the written description. An effect and a characteristic of the disclosure, and a method of accomplishing these will be apparent when referring to embodiments described with reference to the drawings. This disclosure may, however, be embodied in many different forms and should not be construed as limited to the example embodiments set forth herein.

Hereinafter, the disclosure will be described more fully with reference to the accompanying drawings, in which example embodiments of the disclosure are shown. When description is made with reference to the drawings, like reference numerals in the drawings denote like or corresponding elements, and repeated description thereof will be omitted.

As used herein, the singular forms "a", "an" and "the" are intended to include the plural forms as well, unless the context clearly indicates otherwise.

It will be further understood that the terms "comprises/includes" and/or "comprising/including" used herein specify the presence of stated features or components, but do not preclude the presence or addition of one or more other features or components.

When a certain embodiment may be implemented differently, a specific process order may be performed differently from the described order. For example, two consecutively described processes may be performed substantially at the same time or performed in an order opposite to the described order.

Sizes of elements in the drawings may be exaggerated for convenience of explanation. In other words, since sizes and thicknesses of components in the drawings are arbitrarily illustrated for convenience of explanation, the following embodiments are not limited thereto.

FIG. 1 is an exploded perspective view of a liquid medicine injection device according to an embodiment.

Referring to FIG. 1, the liquid medicine injection device may include a first case 110 in an upper portion and a second case 120 in a lower portion coupled to each other. The first case 110 is a portion that is exposed to a user even after the liquid medicine device is mounted on a body of a patient (referred to as the user, hereinafter), and an opening 111 is formed in a partial portion of the first case 110. A button unit 130 passes through the opening 111 and may be exposed to the user.

The button unit 130, a liquid medicine storage unit 140, a pump 150, a needle unit 160, an inner frame 170, a power unit 180, and a circuit unit 190, which is a controller, may be located between the first and second cases 110 and 120 coupled to each other, that is, inside the case.

The liquid medicine storage unit 140 includes a cylinder 141 including a cavity therein, and a piston moving inside the cylinder 141. The inside of the cylinder 141 is the cavity and corresponds to a space in which liquid medicine is stored, and the liquid medicine stored in the inside of the cylinder 141 is discharged to the outside through a discharge hole 145 arranged in one side of the cylinder 141.

The liquid medicine may include liquid including drug, for example, insulin. Alternatively, the liquid medicine may include antibiotic, nutritional supplement, total parenteral nutrition (TPN), painkiller, morphine, hormone, gene therapy medicine, anticoagulant, cardiovascular drug medicine, chemotherapy, or AZT. Kinds of diseases that may be cured by using the liquid medicine injection device may include diabetes, cardiovascular disorder, pain, chronic pain, cancer, AIDS, neurological disorder, Alzheimer's disease, Lou Gehrig's disease, hepatitis, Parkinson's disease, and cramps. However, embodiments are not limited to these liquid medicines and diseases.

The liquid medicine storage unit 140 may be connected to the pump 150 through a first tube TU1 connected to the discharge hole 145. The pump 150 pumps the liquid medicine inside the liquid medicine storage unit 140 toward the needle unit 160. The pump 150 may pump a constant amount of the liquid medicine according to a constant period. The pump 150 may be electrically connected to the power unit 180 (e.g. a battery) and may be electrically connected to the circuit unit 190 and operated by the circuit unit 190.

For the pump 150, all kinds of pumps having liquid medicine sucking force and liquid medicine discharging force by using electricity may be used. For example, all kinds of pumps such as a mechanical displacement-type micro-pump and an electromagnetic motion-type micro-pump may be used. The mechanical displacement-type micro-pump is a pump that uses a motion of solid or fluid such as a gear or a diaphragm to generate a pressure difference so as to induce flow of fluid. The mechanical displacement-type micro-pump may include a diaphragm displacement pump, a fluid displacement pump, or a rotary pump. The electromagnetic motion-type micro-pump is a pump that uses energy in an electric or magnetic form directly for movement of fluid. The electromagnetic motion-type micro-pump may include an electro hydrodynamic pump (EHD), an electro osmotic pump, a magneto hydrodynamic pump, or an electro wetting pump.

The needle unit 160 may be fluidly connected to the pump 150 through a second tube TU2. The liquid medicine may progress toward the needle unit 160 by using liquid medicine discharging force of the pump 150. The needle unit 160 may include a holder 161 that supports a needle 162 and may be arranged in an area defined by a rib 125 of the second case 120. An opening is formed in the area defined by the rib 125 and is smaller than the area. The needle unit 160 may protrude toward the outside through the opening of the second case 120 such that the needle 162 is inserted into a patient's skin.

The inner frame 170 is arranged between the first and second cases 110 and 120. The inner frame 170 may regulate a location of the liquid medicine storage unit 140 in cooperation with the second case 120. For example, first ribs 121 are arranged on the second case 120, the first ribs 121 directly contacting an outer surface of the liquid medicine storage unit 140, for example, at least one of first and second electrodes 211 and 212. Second ribs (not shown) are arranged on locations of the inner frame 170 that face the first ribs 121 of the second case 120 and may regulate the location of the liquid medicine storage unit 140.

The inner frame 170 may regulate a location of a connection structure of the first and second tubes TU1 and TU2, the pump 150, and the needle unit 160. For example, recesses having shapes corresponding to the connection structure of the first and second tubes TU1 and TU2, the pump 150, and the needle unit 160 are formed in the inner frame 170 and thus may receive these elements. Also, the power unit 180 and the circuit unit 190 may be arranged in a space between the inner frame 170 and the second case 120 and thus locations thereof may be regulated.

The power unit 180 is arranged between the inner frame 170 and the second case 120 and provides power to elements of the liquid medicine injection device, for example, the pump 150 and the circuit unit 190.

The circuit unit 190 includes a substrate including circuit wirings. The circuit unit 190 is arranged between the inner frame 170 and the second case 120. The second case 120 may include a rib 122 arranged between the liquid medicine storage unit 140 and the circuit unit 190. The liquid medicine storage unit 140 and the circuit unit 190 may be spaced apart from each other by the rib 122.

The first electrode 211 and the second electrode 212 are arranged on the outer surface of the liquid medicine storage unit 140. Each of the first electrode 211 and the second electrode 212 may continuously extend without including an opening, a hole, or a slit in a movement direction of the piston (or a lengthwise direction of the cylinder). The first electrode 211 and the second electrode 212 may sense a change in a discharged amount of the liquid medicine inside the liquid medicine storage unit 140 depending on movement of the piston during a liquid medicine injection cycle. The liquid medicine inside the liquid medicine storage unit 140 is discharged to the outside by the piston that moves depending on an operation of the pump 150. In this case, an amount of the liquid medicine stored inside the liquid medicine storage unit 140 changes. A change in an amount of the liquid medicine is sensed by a change in a capacitance between the first electrode 211 and the second electrode 212 facing each other around the liquid medicine. A relevant signal is transferred to the circuit unit 190, and the circuit unit 190 may calculate an amount of a change thereof.

Hereinafter, the arrangement of the liquid medicine storage unit 140, and the first and second electrodes 211 and 212, and a sensing principle of the first and second electrodes 211 and 212 are described.

Figure 2:
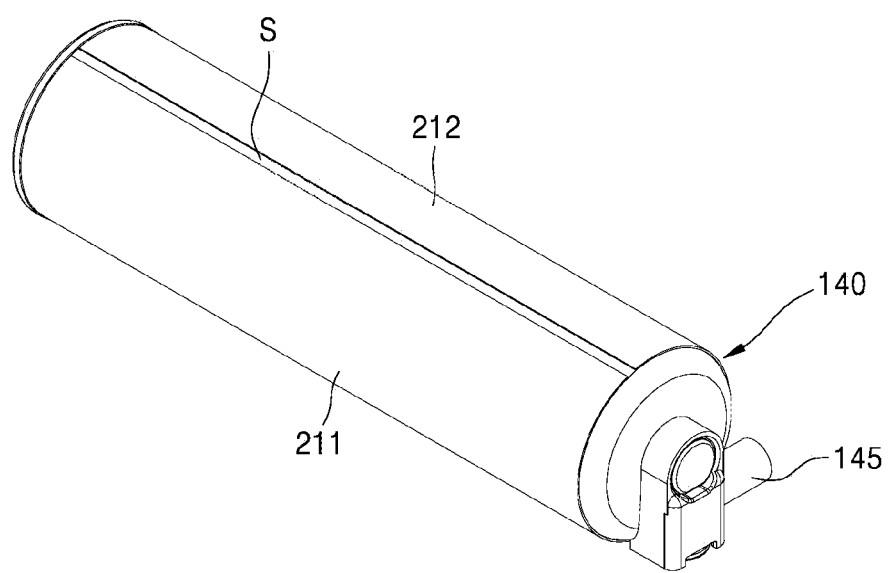
FIG. 2 is a perspective view of a liquid medicine storage unit and a first electrode and a second electrode on an outer surface thereof according to an embodiment.
Figure 3:
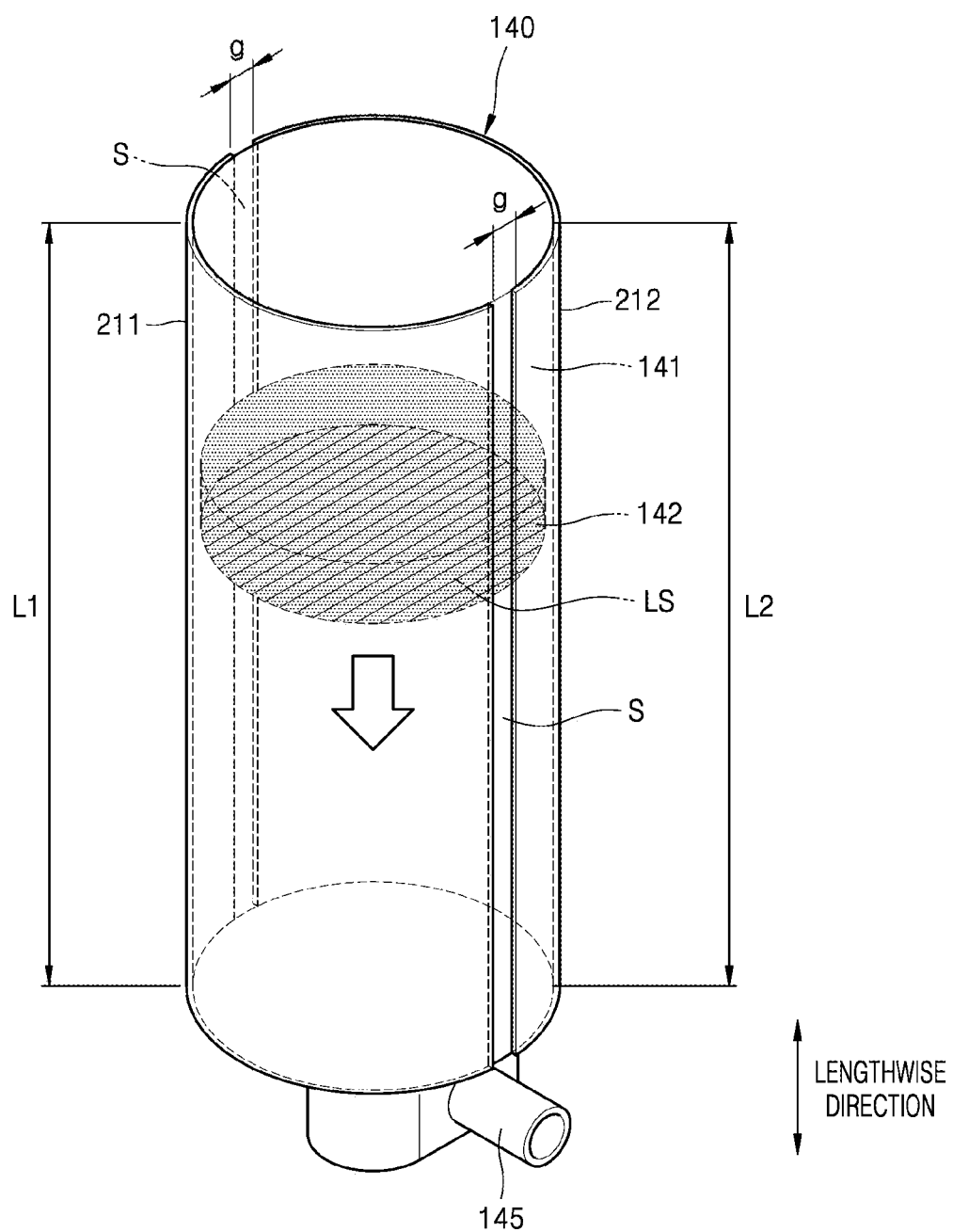
FIG. 3 is a projection perspective view of FIG. 2.

FIG. 2 is a perspective view of the liquid medicine storage unit and the first electrode and the second electrode on an outer surface thereof according to an embodiment, and FIG. 3 is a projection perspective view of FIG. 2.

Referring to FIGS. 2 and 3, the liquid medicine storage unit 140 includes the cylinder 141 including a cavity therein, and a piston 142 moving inside the cylinder 141.

The cylinder 141 may have a pillar shape having a constant cross-section. For example, the cylinder 141 may be formed in a circular cylindrical shape. Alternatively, the cylinder 141 may have various shapes such as an elliptical cylindrical shape or a polygonal pillar shape such as a quadrangular pillar shape. In an embodiment, the cylinder 141 may have a length of about 30 mm to about 35 mm. The cylinder 141 may include an insulating material such as a resin material.

The piston 142 moves toward the discharge hole 145 in the lengthwise direction of the cylinder 141. The piston 142 moves while contacting an inner surface of the cylinder 141. As the piston 142 moves, the liquid medicine stored in the inner space may be discharged to the outside of the cylinder 141 through the discharge hole 145. The piston 142 may include a material such as rubber and/or silicone. When the liquid medicine is discharged to the outside of the cylinder 141 through the discharge hole 145, the piston 142 may move to the discharge hole 145 in proportion to the discharged amount of the liquid medicine. The product of a distance (displacement) by which the piston 142 has moved and an inner cross-section of the cylinder 141 may correspond to a volume of the discharged liquid medicine.

The first electrode 211 and the second electrode 212 are arranged on the outer surface of the cylinder 141 such that the first electrode 211 and the second electrode 212 face each other with the piston 142 therebetween. For example, the first electrode 211 and the second electrode 212 directly contact the outer surface of the cylinder 141 and are spaced apart from each other by a predetermined interval "g" by a slit S extending long in the lengthwise direction. The slit S may be formed by laser cutting, etc. For example, the first electrode 211 and the second electrode 212 spaced apart from each other on the outer surface of the cylinder 141 may be formed by forming a sheet including a conductive material, which will be described below, on the outer surface of the cylinder 141 such that the sheet directly contacts the outer surface of the cylinder 141, and then performing the laser cutting to form the slit S.

Though the first electrode 211 and the second electrode 212 may include a transparent conductive material such as ITO, the present disclosure is not limited thereto. In another embodiment, the first electrode 211 and the second electrode 212 may include a metal material such as copper, aluminium, titanium, molybdenum, or an alloy thereof.

A surface of the first electrode 211 and the second electrode 212 extends in a direction that intersects with a liquid surface LS of the liquid medicine that contacts the piston 142. The first electrode 211 and the second electrode 212 have a substantially constant width and extend in the lengthwise direction of the cylinder 141. For example, one end of the first electrode 211 is arranged adjacent to the discharge hole 145, and another end of the first electrode 211 extends in the lengthwise direction of the cylinder 141 such that the other end of the first electrode 211 is away from the discharge hole 145. Likewise, one end of the second electrode 212 is arranged adjacent to the discharge hole 145, and another end of the second electrode 212 extends in the lengthwise direction of the cylinder 141 such that the other end of the second electrode 212 is away from the discharge hole 145.

The liquid medicine injection device according to embodiments is designed to sense discharge of the liquid medicine by using electrode sheets of the first and second electrodes 211 and 212, and continuously extends in the lengthwise direction of the cylinder 141 as described above. In an embodiment, lengths L1 and L2 respectively of the first and second electrodes 211 and 212 may be 0.7 times greater than the length of the cylinder 141. The lengths L1 and L2 respectively of the first and second electrodes 211 and 212 may be 0.72 times or more of the length of the cylinder 141, 0.75 times or more of the length of the cylinder 141, 0.8 times or more of the length of the cylinder 141, 0.82 times or more of the length of the cylinder 141, 0.85 times or more of the length of the cylinder 141, 0.9 times or more of the length of the cylinder 141, 0.92 times or more of the length of the cylinder 141, 0.95 times or more of the length of the cylinder 141, or 0.98 times or more of the length of the cylinder 141. In another embodiment, the lengths L1 and L2 respectively of the first and second electrodes 211 and 212 may substantially the same as the length of the cylinder 141.

For a sensing performance (e.g. resolution) of the first and second electrodes 211 and 212, which will be described below with reference to FIGS. 4A and 4B, a sum of widths of the first and second electrodes 211 and 212 that are perpendicular to the lengthwise direction may be less than an outer circumference ($\pi d$) of the cylinder 141. The sum may be equal to or greater than 0.85 times of the outer circumference, equal to or greater than 0.88 times of the outer circumference, or equal to or greater than 0.90 times of the outer circumference, but the present disclosure is not limited thereto.

Figure 4A:
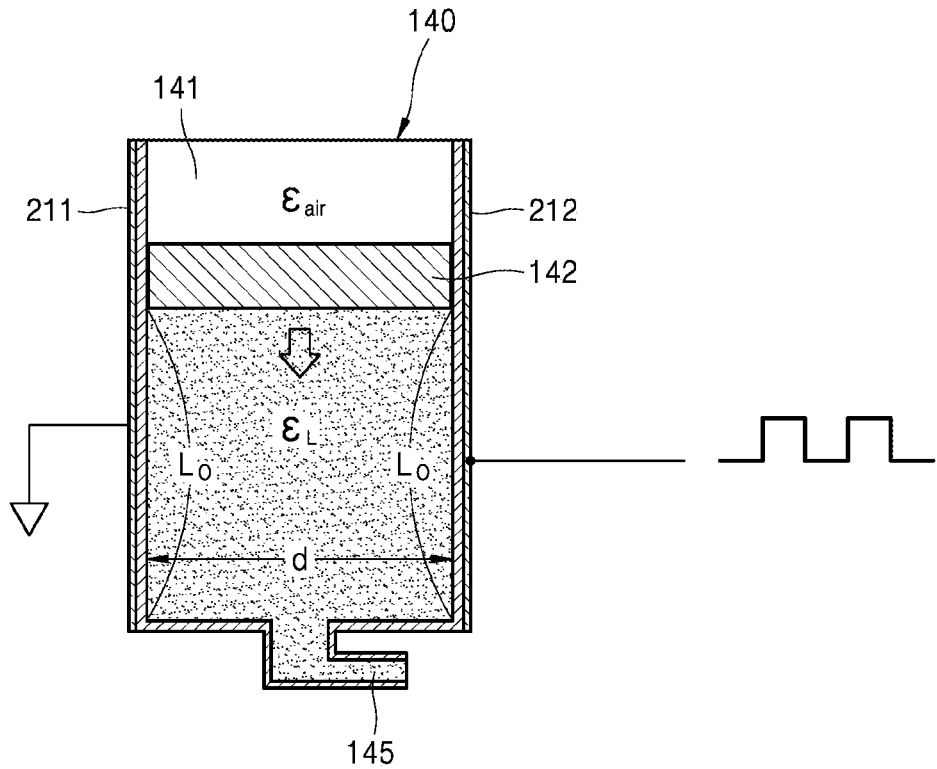
FIGS. 4A and 4B are conceptual views of a sensing principle of first and second electrodes depending on liquid medicine injection.
Figure 4B:
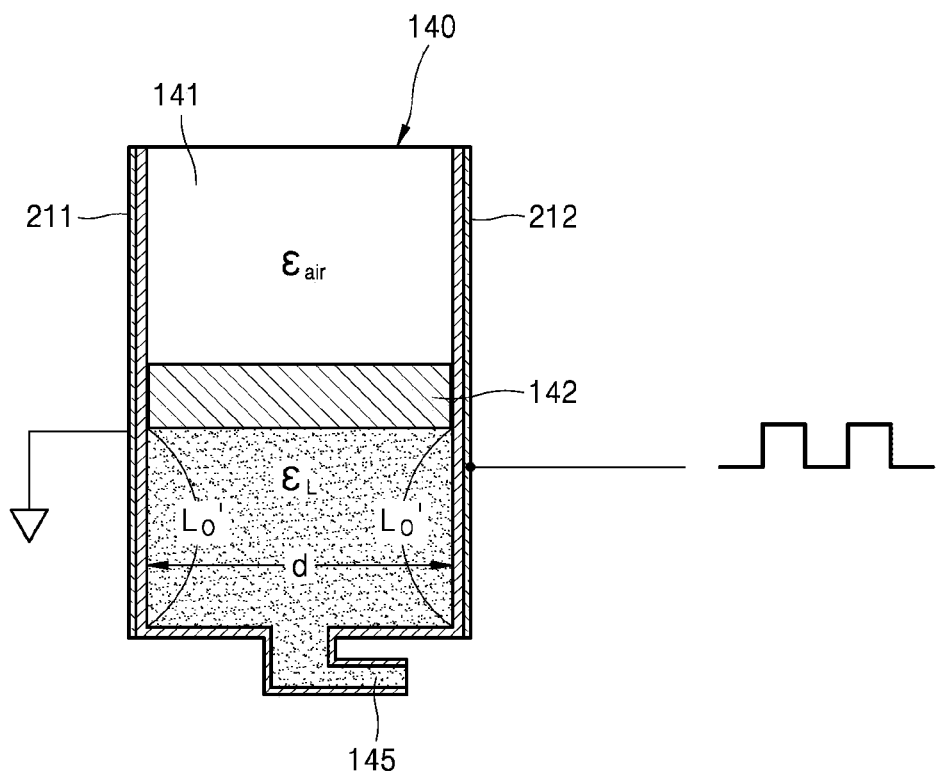

FIGS. 4A and 4B are conceptual views of a sensing principle of the first and second electrodes depending on liquid medicine injection. For convenience of description, a location of the piston 142 in FIG. 4A is referred to as a first location, and a location of the piston 142 in FIG. 4B is referred to as a second location.

Referring to FIG. 4A, at the first location of the piston 142, air, the piston 142, and the liquid medicine are located between the first electrode 211 and the second electrode 212. A factor that substantially influences a capacitance between the first electrode 211 and the second electrode 212 is liquid medicine. That is, the capacitance C between the first electrode 211 and the second electrode 212 is determined, as Equation below, by a dielectric constant $\epsilon_L$ of the liquid medicine and an area A of the first electrode 211 and the second electrode 212 facing each other with the liquid medicine therebetween. Since a width W of the first electrode 211 and the second electrode 212 and a distance d between the first electrode 211 and the second electrode 212 are constant, the area A is determined by the length Lo.

$$C = \epsilon_L A/d = \epsilon_L L_o \times w/d$$

That is, the capacitance C is proportional to the dielectric constant $\epsilon_L$ and the length Lo of the first electrode 211 and the second electrode 212 facing each other with the liquid medicine therebetween. Since the dielectric constant $\epsilon_L$ of the liquid medicine has a constant value, the capacitance C depends on the length Lo of the first electrode 211 and the second electrode 212 facing each other with the liquid medicine therebetween.

Likewise, as shown in FIG. 4B, at the second location of the piston 142, a capacitance C' between the first electrode 211 and the second electrode 212 depends on a length Lo' of the first electrode 211 and the second electrode 212 facing each other with the liquid medicine therebetween.

The circuit unit 190 calculates a height difference Lo-Lo' of the liquid medicine, that is, displacement information, which is a movement distance of the piston 142, depending on a change in the capacitance. Since the lengths Lo and Lo' of the first electrode 211 and the second electrode 212 facing each other and overlapping the liquid medicine change when the liquid medicine is discharged, even when the same pulse signal is applied, a difference between pulse response signals occurs, and the height difference Lo-Lo' of the liquid medicine (or the displacement of the piston 142) may be calculated through the difference between the pulse response signals.

In an embodiment, each of the first and second electrodes 211 and 212 is electrically connected to the circuit unit 190. For example, the first electrode 211 serves as a ground, and a pulse signal may be applied to the second electrode 212 by the circuit unit 190. As described above, since a change in the capacitance between the first and second electrodes 211 and 212 is caused by the discharge of the liquid medicine, the circuit unit 190 may calculate a height difference of the liquid medicine (or the displacement of the piston 142) and an actual discharge amount of the liquid medicine based on a pulse response signal, and control discharge of the liquid medicine based on this.

Figure 5:
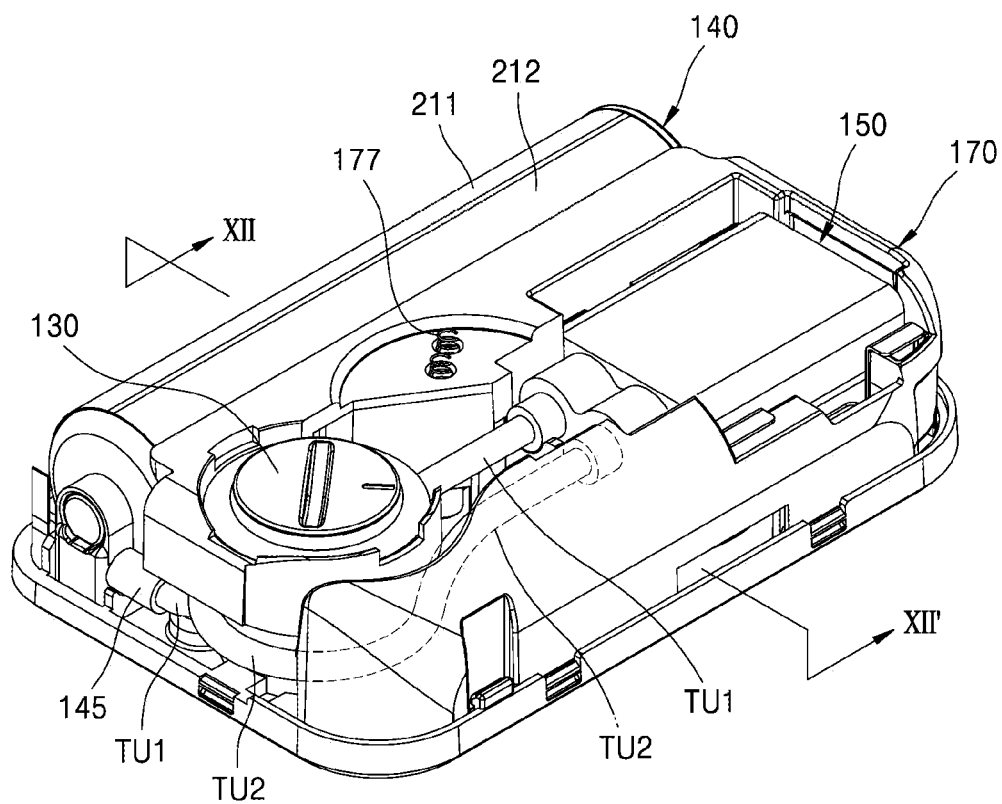
FIG. 5 is a perspective view of a liquid medicine injection device with a first case omitted according to an embodiment.
Figure 6:
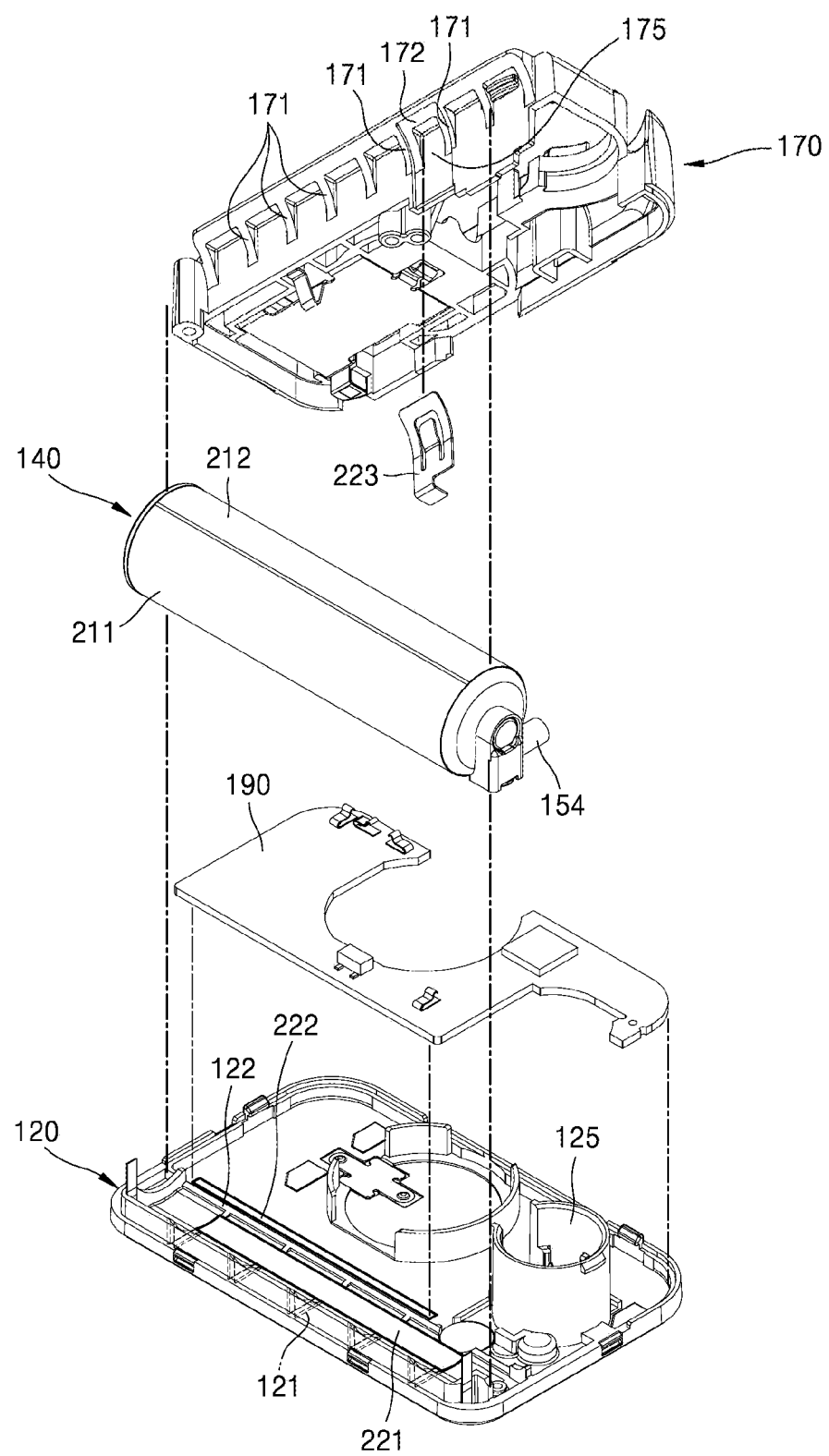
FIG. 6 is an extracted exploded perspective view of a second case, a liquid medicine storage unit, an inner frame, and a circuit unit of FIG. 5.
Figure 7:
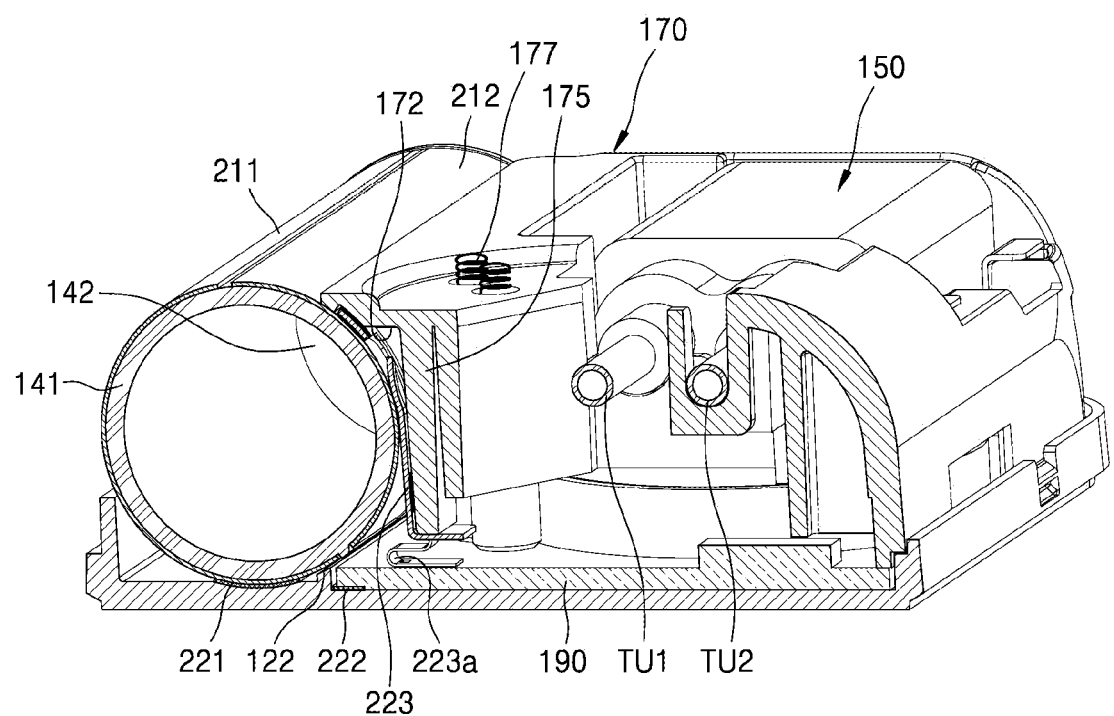
FIG. 7 shows a cross-section taken along line VII-VII of FIG. 5.

FIG. 5 is a perspective view of a liquid medicine injection device with the first case omitted according to an embodiment, FIG. 6 is an extracted exploded perspective view of the second case, the liquid medicine storage unit, the inner frame, and the circuit unit of FIG. 5, and FIG. 7 shows a cross-section taken along line VII-VII of FIG. 5.

Referring to FIGS. 5 to 7, the liquid medicine storage unit 140 on the outer surface of which the first and second electrodes 211 and 212 are arranged may be arranged on one side of the second case 120, and other elements, for example, the circuit unit 190, the inner frame 170, the button unit 130, and the pump 150 connected to the liquid medicine storage unit 140 and the needle unit 160 (see FIG. 1) through the first and second tubes TU1 and TU2 may overlap each other on another side of the second case 120.

As shown in FIG. 6, a location of the liquid medicine storage unit 140 may be regulated by the first ribs 121 arranged on the second case 120 and second ribs 171 of the inner frame 170, the first ribs 121 and the second ribs 171 facing each other. For example, the first ribs 121 of the second case 120 may be arranged on a lower end on one side of the liquid medicine storage unit 140, the second ribs 171 of the inner frame 170 may be arranged on an upper end on another side of the liquid medicine storage unit 140, the first ribs 121 of the second case 120 may contact the first electrode 211, and the second ribs 171 of the inner frame 170 may contact the second electrode 212. An elastic member 177 (see FIGS. 5 and 7) such as a spring may be arranged between the inner frame 170 and the first case 110 to prevent the inner frame 170 from being destroyed inside the first and second cases 110 and 120 during a situation such as shaking of the liquid medicine injection device, etc.

The first electrode 211 is electrically connected to the circuit unit 190. For example, the first electrode 211 may be electrically connected to the circuit unit 190 by the medium of the second case 120. In an embodiment, the first electrode 211 may be connected to the second case 120 by a first conductive member 221 between the first electrode 211 and the second case 120, the first conductive member 221 contacting the first electrode 211 and the second case 120. The second case 120 may be connected to the circuit unit 190 by a second conductive member 222 between the second case 120 and the circuit unit 190, the second conductive member 222 contacting the second case 120 and the circuit unit 190. In this case, the second case 120 may include a conductive material. That is, the first electrode 211 may be electrically connected to the circuit unit 190 by the first and second conductive members 221 and 222 by the medium of the second case 120. The first and second conductive members 221 and 222 may include conductive paste or a conductive double-sided tape.

Though FIGS. 6 and 7 show the structure in which the first electrode 211 and the circuit unit 190 are connected to each other by the first and second conductive members 221 and 222, the first electrode 211 and the circuit unit 190 are connected to each other by one conductive member in another embodiment. In this case, one conductive member may include the above-mentioned conductive paste, conductive double-sided tape, or wire.

As shown in FIGS. 6 and 7, the second electrode 212 may be connected to the circuit unit 190 by a third conductive member 223. An end 223a of the third conductive member 223 may directly contact the circuit unit 190. The third conductive member 223 may have a shape curved along the outer surface of the liquid medicine storage unit 140 on which the second electrode 212 is arranged and may be arranged between the second ribs 171 that are adjacent to each other.

A location of the third conductive member 223 may be regulated by the inner frame 170. For example, a portion of the third conductive member 223 may be received in a recess 172 formed in the inner frame 170. The recess 172 may be arranged between the second ribs 171 that are adjacent to each other.

The third conductive member 223 may be covered by a partition wall 175 corresponding to the recess 172 to prevent a location breakaway of the third conductive member 223 by the other elements (e.g. the pump, the battery, the tube, etc.). The third conductive member 223 may be protected by the partition wall 175 between the second electrode 212 and the partition wall 175, and simultaneously, pressurized to stably maintain a contact with the second electrode 212.

Although the disclosure has been described with reference to the embodiments illustrated in the drawings, this is merely provided as an example and it will be understood by those of ordinary skill in the art that various changes in form and details and equivalents thereof may be made therein without departing from the spirit and scope of the disclosure as defined by the following claims.

What is claimed is:

1. A liquid medicine injection device comprising:
   a liquid medicine storage unit including:
      a cylinder including a space configured to store liquid medicine therein,
      a discharge hole connected to the space, and
      a piston arranged inside the cylinder and configured to move toward the discharge hole depending on discharge of the liquid medicine when present;
   a first electrode on an outer surface of the cylinder;
   a second electrode on the outer surface of the cylinder, the second electrode facing the first electrode with the piston therebetween;
   a circuit unit electrically connected to the first electrode and the second electrode;
   a case configured to receive the liquid medicine storage unit and the circuit unit;
   a first conductive member located at an inner surface of the case and being along an outer surface of the liquid medicine storage unit, the first conductive member being electrically connected to the first electrode; and
   a second conductive member electrically connected to the second electrode,
   wherein the first electrode serves as a ground, and the second electrode is configured to receive a pulse signal applied by the circuit unit,
   wherein the circuit unit is configured to calculate displacement information of the piston based on a capacitance change between the first electrode and the second electrode due to a difference between pulse response signals, and to thereby calculate an actual injected amount of the liquid medicine based on the displacement information of the piston,
   wherein the first electrode is electrically connected to the circuit unit by the first conductive member,
   wherein the second electrode is electrically connected to the circuit unit by the second conductive member, and
   wherein at least one of the first conductive member or the second conductive member stably contacts at least one of the first electrode or the second electrode by an elastic force of an elastic member disposed inside the case.

2. The liquid medicine injection device of claim 1, wherein the first electrode and the second electrode extend in a direction that intersects with a liquid surface of the liquid medicine that contacts the piston.

3. The liquid medicine injection device of claim 1, wherein one end of the first electrode is adjacent to the discharge hole, and another end of the first electrode extends away from the discharge hole, and
   one end of the second electrode is adjacent to the discharge hole, and another end of the second electrode extends away from the discharge hole.

4. The liquid medicine injection device of claim 1, wherein the elastic member is arranged between the case and an inner frame.

5. The liquid medicine injection device of claim 1, wherein the first conductive member contacts the inner surface of the case.

6. The liquid medicine injection device of claim 1, further comprising a pump connected to the discharge hole.

7. The liquid medicine injection device of claim 1, wherein the case includes first ribs arranged in a lengthwise direction of the liquid medicine storage unit, and an inner frame includes second ribs facing the first ribs of the case with the liquid medicine storage unit between the first ribs and the second ribs.

8. The liquid medicine injection device of claim 1, wherein the second conductive member has a shape curved along the outer surface of the liquid medicine storage unit.

9. The liquid medicine injection device of claim 8, further comprising an inner frame inside the case, wherein the inner frame is configured to regulate a location of the first conductive member or the second conductive member.

* * * * *